United States Patent
Dumeunier et al.

(10) Patent No.: US 9,637,457 B2
(45) Date of Patent: May 2, 2017

(54) PROCESS FOR THE STEREOSELECTIVE PREPARATION OF A PYRAZOLE-CARBOXAMIDE

(71) Applicant: Syngenta Participations AG, Basel (CH)

(72) Inventors: Raphael Dumeunier, Stein (CH); Jilali Kessabi, Stein (CH); Sebastian Volker Wendeborn, Stein (CH); Hannes Nussbaumer, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/892,386

(22) PCT Filed: Jun. 19, 2014

(86) PCT No.: PCT/EP2014/062936
§ 371 (c)(1),
(2) Date: Nov. 19, 2015

(87) PCT Pub. No.: WO2014/206855
PCT Pub. Date: Dec. 31, 2014

(65) Prior Publication Data
US 2016/0108001 A1    Apr. 21, 2016

(51) Int. Cl.
*C07D 231/14* (2006.01)
*C07C 239/20* (2006.01)

(52) U.S. Cl.
CPC .......... *C07D 231/14* (2013.01); *C07C 239/20* (2013.01)

(58) Field of Classification Search
None
See application file for complete search history.

(56) References Cited

U.S. PATENT DOCUMENTS 8,258,169 B2 * 9/2012 Rajan ................ A01N 43/56
514/406

FOREIGN PATENT DOCUMENTS

WO    2010063700 A2    6/2010
WO    2012041874 A1    4/2012

OTHER PUBLICATIONS

Krzeminski, Marek P. et al: "Asymmetric reduction of ketoxime derivatives and N-alkylketimines with borane-oxazaborolidine adducts" in: Tetrahedron. Asymmetry 14 (2003), Pergamon, pp. 1463-1466.

(Continued)

*Primary Examiner* — Kamal Saeed
(74) *Attorney, Agent, or Firm* — R. Kody Jones

(57) ABSTRACT

The present invention relates to a process for the enantioselective preparation of the compound of formula (Ib), which process comprises a) reducing the (E)- or (Z)-form of a compound of formula (II), with an enantioselective reagent to a compound of formula (IIIa), and b) acylating the compound of formula (IIIa) with the compound of formula (IV), or c) coupling the compound of formula (IV) with the compound of formula (II), to give a compound of formula (V) and d) reducing compound of formula (V) in the presence of hydrogen, a catalyst and a chiral ligand, to the compound of formula (Ib).

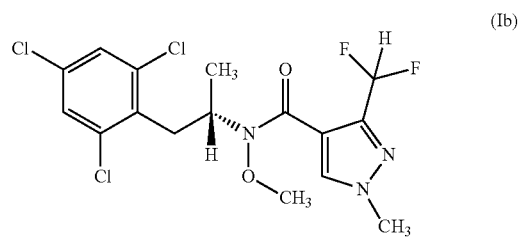

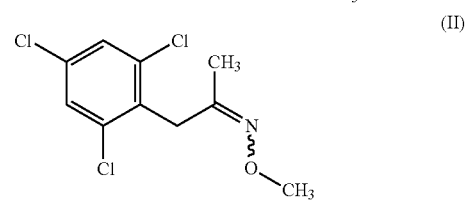

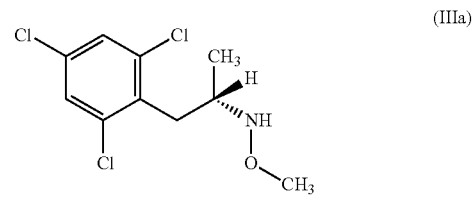

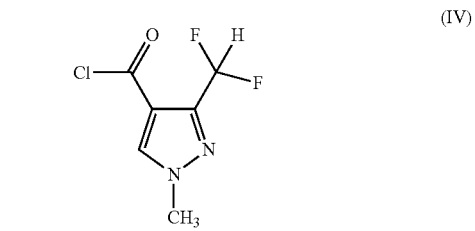

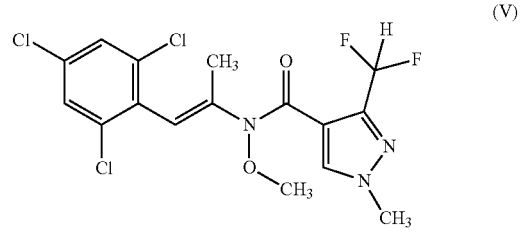

7 Claims, No Drawings

(56) References Cited

OTHER PUBLICATIONS

Laczkowski, Krzysztof Z.: "Asymmetric synthesis of N-substituted N-hydroxyureas" in: Tetrahedron. Asymmetry 19 (2008), Elsevier, pp. 788-795.
Bosiak, Mariusz J. et al.: "Asymmetric synthesis of N-1-(heteroaryl)ethyl-N-hydroxyureas" in: Tetrahedron. Asymmetry 19 (2008), Elsevier, pp. 956-963.
Lantos, Ivan et al.: "Enantioselective Synthesis of 5-LO Inhibitor Hydroxyureas. Tandem Nucleophilic Addition-Intramolecular Cyclization of Chiral Nitrones" in: J. Org. Chem. 62 (1997), pp. 5385-5391.
Dougherty, John T.: "Asymmetric reduction of ketoxime ethers to optically active Osubstituted hydroxylamines with reagents prepared from borane and chiral amino alcohols" in: Tetrahedron. Asymmetry 8/4 (1997), Pergamon, pp. 497-499.
Fontaine, Evelyne et al.: "Synthesis of optically-active benzylic amines; asymmetric reduction of ketoxime ethers with chiral oxazaborolidines" in: Tetrahedron. Asymmetry 12 (2001), Pergamon, pp. 2185-2189.
Dutheuil, Guillaume et al.: "First enantioselective reductive amination of a-fluoroenones" in: J. of Fluorine Chemistry 128 (2007), Elsevier, pp. 34-39.
Itsuno et al—Asymmetric Syntheses using Chirally Modified Borohydrides. Part 3. Enantioselective REductin of Ketones and Oxime Ethers with REagents Prepared from Borane and Chiral Amino Alcohols—J Chem Soc Perkin Trans 1985 (p. 2039-2044).
EP Search Report mailed Aug. 22, 2013 for EP Appln 13173724.9.
International Search Report mailed Aug. 7, 2014 for International Patent Application No. PCT/EP2014/062936.

* cited by examiner

PROCESS FOR THE STEREOSELECTIVE PREPARATION OF A PYRAZOLE-CARBOXAMIDE

RELATED APPLICATION INFORMATION

This application is a 371 of International Application No. PCT/EP2014/062936, filed 19 Jun. 2014, which claims priority to EP Patent Application No. 13173724.9, filed 26 Jun. 2013, the contents of which are incorporated by reference herein.

The present invention relates to a process for the stereoselective (enantioselective) preparation of 3-(difluoromethyl)-N-methoxy-1-methyl-N-[1-methyl-2-(2,4,6-trichlorophenyl)ethyl]pyrazole-4-carboxamide.

The compound 3-(difluoromethyl)-N-methoxy-1-methyl-N-[1-methyl-2-(2,4,6-trichlorophenyl)ethyl]pyrazole-4-carboxamide is described for example in WO 2010/063700. Said compound shows an excellent fungicidal activity.

Said compound can occur in two enantiomeric forms, the form of the formula Ia

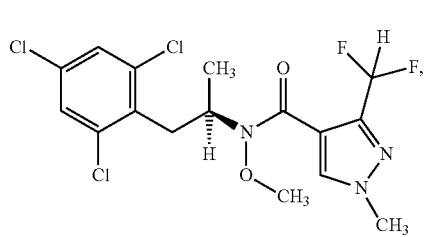

which chemical designation is 3-(difluoromethyl)-N-methoxy-1-methyl-N-[(1R)-1-methyl-2-(2,4,6-trichlorophenyl)ethyl]pyrazole-4-carboxamide, and the form of the formula Ib

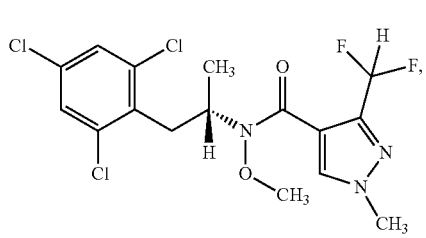

which chemical designation is 3-(difluoromethyl)-N-methoxy-1-methyl-N-[(1S)-1-methyl-2-(2,4,6-trichlorophenyl)ethyl]pyrazole-4-carboxamide.

The enantiomer of formula Ib shows a more prominent fungicidal activity. A fungicide with an excess of the fungicidally more active enantiomer can be applied in lower concentrations with the same efficiency as the racemate which is economically advantageous. It is therefore highly desired to selectively prepare the Ib-enantiomer of said compound.

It is known from WO 2010/063700 to prepare the racemic form of 3-(difluoromethyl)-N-methoxy-1-methyl-N-[1-methyl-2-(2,4,6-trichlorophenyl)ethyl]pyrazole-4-carboxamide by a) reducing the compound of formula II

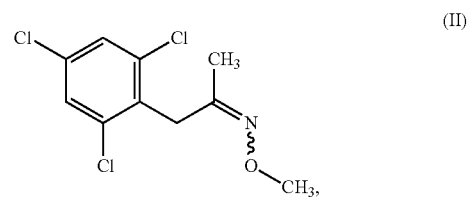

in the presence of a reducing agent to the compound of formula III

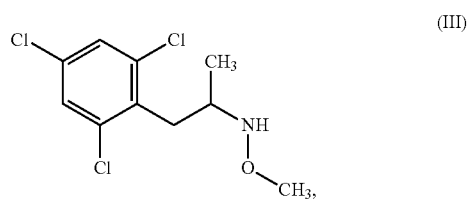

and
b) reacting the compound of formula III with the compound of formula IV

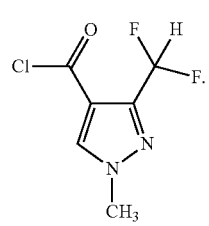

The product of this process is 3-(difluoromethyl)-N-methoxy-1-methyl-N-[1-methyl-2-(2,4,6-trichlorophenyl)ethyl]pyrazole-4-carboxamide in form of the racemate.

The two enantiomers of 3-(difluoromethyl)-N-methoxy-1-methyl-N-[1-methyl-2-(2,4,6-trichlorophenyl)ethyl]pyrazole-4-carboxamide can be separated for example by chiral chromatography of the racemate. However, said method is expensive and unsuitable for large-scale production of said compound.

The compound of formula III was prepared according to WO 2010/063700 in racemic form. It has been found that the 3-(difluoromethyl)-N-methoxy-1-methyl-N-[(1S)-1-methyl-2-(2,4,6-trichlorophenyl)ethyl]pyrazole-4-carboxamide (enantiomer of formula Ib) can be produced by this process in excess to 3-(difluoromethyl)-N-methoxy-1-methyl-N-[(1R)-1-methyl-2-(2,4,6-trichlorophenyl)ethyl]pyrazole-4-carboxamide (enantiomer of formula Ia) if the enantioselective step is the enantioselective synthesis of the compound of formula III, so that the enantiomer (2S)—N-methoxy-1-(2,4,6-trichlorophenyl)propan-2-amine of formula IIIa

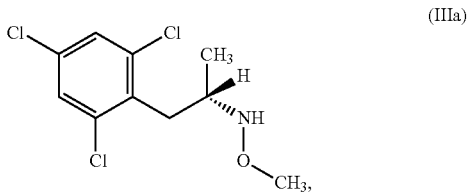

is obtained in excess. The enantioselective synthesis of the compound of formula III allows a very cost effective preparation of the fungicide 3-(difluoromethyl)-N-methoxy-1-methyl-N-[(1S)-1-methyl-2-(2,4,6-trichlorophenyl)ethyl]pyrazole-4-carboxamide with high yields.

Alternatively, it is possible to prepare the compound 3-(difluoromethyl)-N-methoxy-1-methyl-N-[(1S)-1-methyl-2-(2,4,6-trichlorophenyl)ethyl]pyrazole-4-carboxamide by c) coupling the compound of formula IV with the compound of formula II, to give a compound of formula V

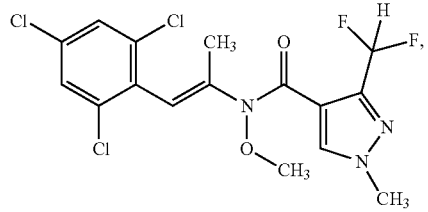

(V)

and d) reducing the compound of formula V in the presence of hydrogen, a catalyst and a chiral ligand, to the compound of formula Ib.

The aim of the present invention is therefore to provide a novel process for the enantioselective preparation of 3-(difluoromethyl)-N-methoxy-1-methyl-N-[(1S)-1-methyl-2-(2,4,6-trichlorophenyl)ethyl]pyrazole-4-carboxamide of formula Ib

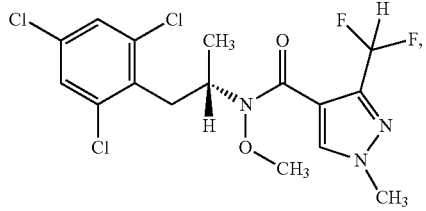

(Ib)

which process comprises a) reducing the (E)- or (Z)-form of a compound of formula II

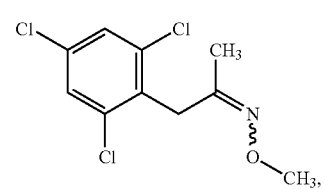

(II)

with an enantioselective reagent to a compound of formula IIIa

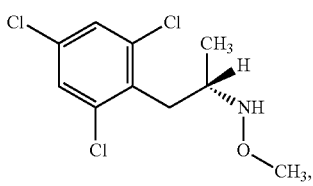

(IIIa)

and b) acylating the compound of formula IIIa with the compound of formula IV

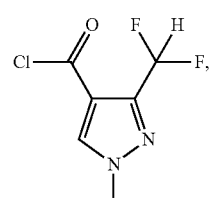

(IV)

or c) coupling the compound of formula IV with the compound of formula II, to give a compound of formula V

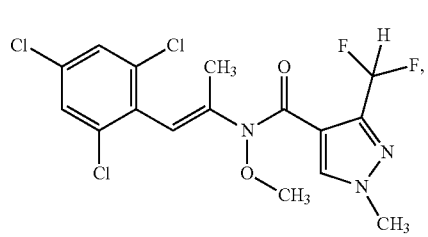

(V)

and d) reducing the compound of formula V in the presence of hydrogen, a catalyst and a chiral ligand, to the compound of formula Ib.

The product of this process is 3-(difluoromethyl)-N-methoxy-1-methyl-N-[1-methyl-2-(2,4,6-trichlorophenyl)ethyl]pyrazole-4-carboxamide I in form of a mixture of formula Ia and Ib, wherein 3-(difluoromethyl)-N-methoxy-1-methyl-N-[(1S)-1-methyl-2-(2,4,6-trichlorophenyl)ethyl]pyrazole-4-carboxamide (Ib) is present in the mixture in an excess of 55-99% to the compound of formula Ia.

According to the present invention, preparation in enantiomerically enriched form or in excess means that the molar proportion of the desired product (formula IIIa and formula Ib) is greater than 50% (for example greater than 55, 60, 65, 70, 75, 80, 85, 90, 95, 96, 97, 98 or 99%) of the total amount of all isomers present in the reaction mixture.

Reaction Step a):

The asymmetric reduction of oxime ethers is described in the literature, but most often it is not to N-alkoxy-amines: the product obtained is the fully reduced amine. This usually requires borane complexes as reducing agents, in the presence of chiral 1,2-amino-alcohols (J. CHEM. SOC. PERKIN TRANS. I, 1985, 2039). The first example of an asymmetric reduction of oxime ethers to N-alkoxy-amines can be found in an article (J. ORG. CHEM., 1997, 5385) describing the use of an asymmetric borane reagent. That same year, the same group published a paper describing the scope of this reaction (TETRAHEDRON: ASYMMETRY, 1997, 497), where the chiral amino-alcohol is used in more than stoichiometric amount (1.32 eq.) and the oxime ether is within a ring and directly connected to an aromatic ring. During the following years, sparse reports describing such reactions appeared, but the reduction always led to mixtures of fully reduced amines and N-Alkoxy-amines, the latter being sometimes the minor component of the mixture (TETRAHEDRON: ASYMMETRY, 2001, 2185; TETRAHEDRON: ASYMMETRY, 2003, 1463; JOURNAL OF FLUORINE CHEMISTRY, 2007, 34; TETRAHEDRON: ASYMMETRY, 2008, 788). These groups always used more than 1eq. of chiral amino alcohol. Only a single report of 2008 reports a similar result as in the seminal discovery (no mixture mentioned), that is, with an oxime ether directly connected to an aromatic ring (Hetero—in this case), with more than stoichiometric amounts of chiral amino-alcohol as the source of asymmetry (1.2eq.), a clean N-alkoxy-amine can be obtained from asymmetric reduction of an oxime ether (TETRAHEDRON: ASYMMETRY, 2008, 956).

From all these references, it was found that (1) a chiral amino-alcohol and a borane complex can be used as the asymmetric reducing agent and usually needs (disadvantageously) to be present in more than stoichiometric amounts to get satisfying enantiomeric excesses and conversions and (2), the oxime ether has to be present either in the (E)- or in the (Z)-form as its configuration will impact greatly the absolute configuration of the amine obtained from reduction. The use of a mixture of (E)- and (Z)-forms of the oxime is therefore not recommended in reaction step a).

It was surprisingly found in connection with the present invention that, advantageously, (1) catalytic amounts of chiral amino-alcohols can be used and maintain good conversions and enantiomeric excesses, (2) by using a borane-diethylaniline complex as the source of borane in the asymmetric reduction of oxime ethers to N-alkoxy-amines, the concomitant formation of undesired amines (fully reduced compound) can be reduced to a few percent or avoided, (3) oximes like compound (II), where the carbon atom of the oxime group is not directly connected to an aromatic or heteroaromatic ring nor is it within a ring, can still be reduced enantioselectively while avoiding the formation of undesired fully reduced amines.

The source of borane may be chosen by the person skilled in the art from the different commercial sources such as, dimethylsulfide, tetrahydrofuran, triethylamine, trimethylamine, diethylaniline complexes. Preferred sources are dimethylsulfide, tetrahydrofuran and diethylaniline complexes, and particularly preferred for stopping at the alkoxy-amine stage in the reduction is the diethylaniline-borane complex. Alternatively, the borane-complex may be prepared in situ by a person skilled in the art from sodium borohydride and, for example, trimethylsilylchloride or dimethylsulfate, followed by its complexation to diethylaniline.

The chiral 1,2-amino-alcohols may be chosen by the person skilled in the art from different sources, in the form of a single enantiomer, for example such as described under the Chemical Abstract Entry Numbers CAS 492-41-1, 126456-43-7, 112068-01-6, 104354-35-0, 2026-48-4, 129704-13-8, 79868-78-3, 144054-70-6, 78603-95-9, 78603-91-5, the structures of which are depicted below:

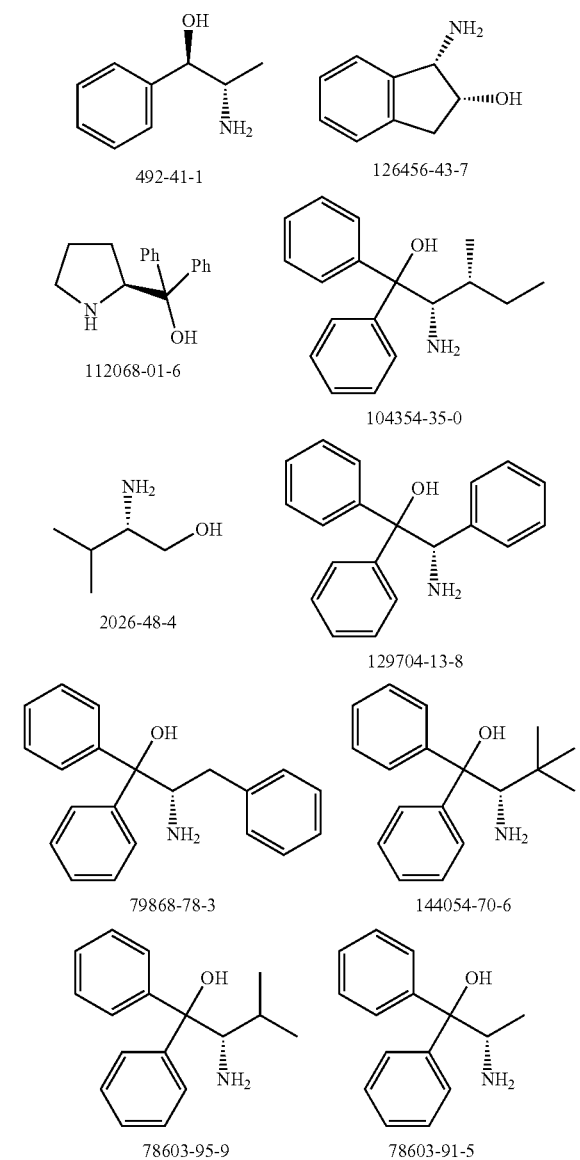

All inert solvents known to the person skilled in the art for this purpose may be used; also mixtures of these solvents in any composition may be used. Preferred classes of solvents include ethers, hydrocarbons, aromatic hydrocarbons, chlorinated hydrocarbons and nitrolalkanes. Particularly preferred solvents according to the invention are selected from the group consisting of tetrahydrofuran, 2-methyl-tetrahydrofuran, diethylether, dioxane, toluene, xylene, chlorobenzene, nitromethane and nitroethane and mixtures of those.

The temperature during the reduction reaction may in principle be chosen arbitrarily by the person skilled in the art as long as a sufficiently quick and selective reaction is achieved. The reaction is accordingly preferably carried out at temperatures between −10° and 100° C., more preferably between 0° and 80° C. and particularly preferably between 25° and 60° C.

Reaction time of the reduction is between 10 minutes and 48 hours, preferably between 30 minutes and 24 hours, most preferably between 1 hour and 12 hours.

The compound of formula IIIa

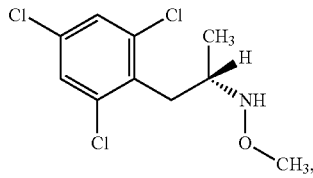

(IIIa)

is novel, is especially developed for the process according to the invention and therefore constitutes a further object of this invention.

In a preferred embodiment of the present invention, the enantioselective reduction of the compound of formula II is performed via the action of borane in the presence of a single enantiomer of a chiral amino-alcohol.

Reaction step b) can be performed analogously as described in WO 2010/063700. The reaction to give compound of formula Ib are advantageously carried out in aprotic inert organic solvents. Such solvents are hydrocarbons such as benzene, toluene, xylene or cyclohexane, chlorinated hydrocarbons such as dichloromethane, trichloromethane, or chlorobenzene, ethers such as dialkylethers, ethylene glycol dimethyl ether, diethyleneglycol dimethyl ether, tetrahydrofuran or dioxane, amides such as N,N-dimethylformamide, diethylformamide or N-methylpyrrolidinone. The reaction temperatures are advantageously between −20° C. and +120° C. In general, the reactions are slightly exothermic, and they can be carried out at ambient temperature. The reaction is usually performed in the presence of a weak base, in particular, tertiary amines such as triethylamine.

Reaction step c) can be performed as follows: While the preparation and use of enamides (compound 100, X═H) is well known in the art, examples for the preparation of N—O-alkyl substituted enamides (compound 100, X═OMe, OAlkyl)

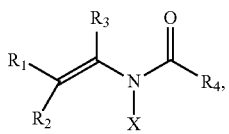

(100)

are rare and also there is no generally applicable procedure is available for the preparation of such compounds. The examples that are reported include: substitution of an N-brominated enamides (compound 100, X═Br) with NaOCH$_3$ (*Bull. Chem. Soc. Jpn.* 1975, 48, 2492). In-situ trifluoro acylation of oximes with (CF$_3$C(O)O)$_2$ in the presence of DMAP (*Eur. J. Org. Chem.* 2007, 1491). Cyclic oxime ethers have been acylated with a number of different acid chlorides (*J. Org. Chem.* 1979, 44, 2487).

Few examples describe the deprotonation of O-alkyl oximes carrying an acidic proton in the alpha position (compound 101, X═OCH$_3$ or O-alkyl) to make the corresponding anionic species (compound 102, X═OCH$_3$, O-alkyl, M═Li, K,)

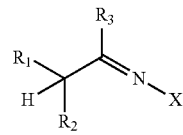

(Comp. 101)

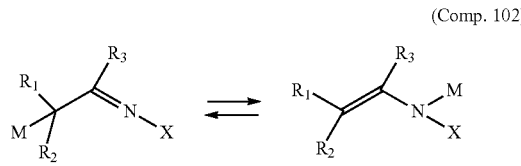

(Comp. 102)

Examples include the use of BuLi (*Liebigs Ann. Chem.* 1991, 189; *Liebigs Ann. Chem.* 1991, 381). KN(iPr)$_2$ has been reported to be a superior reagent when compared to Li(N(iPr)$_2$ and BuLi (*Tetrahedron Lett.* 1980, 21, 3115).

Reaction step c) can be performed by deprotonation of the compound of formula II (single isomer or a mixture of E/Z isomers) with a suitable base (KN(iPr)$_2$, LiN(iPr)$_2$, KN(t-rimethylsilyl)$_2$, BuLi, KN(iPr)$_2$/KOtBu) (1-5 equivalents, preferably 2 equivalents) in a suitable inert aprotic solvent (such as benzene, toluene, xylene or cyclohexane, ethers such as dialkylethers, ethylene glycol dimethyl ether, diethyleneglycol dimethyl ether, tetrahydrofuran or dioxane) at a suitable temperature (−78° C. to 20° C., solvent dependent). The anion generated this way is treated with the compound VI to give the compound V. The reaction may be performed in batch or in flow or a combination of the two.

The compound of formula V

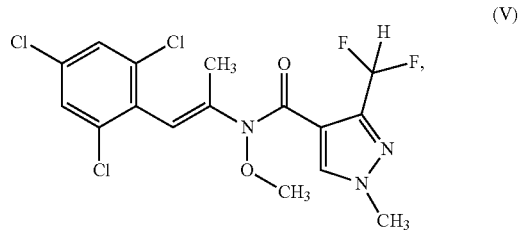 [SMILES: CON(C(=O)c1cn(C)nc1C(F)F)/C(C)=C/c1c(Cl)cc(Cl)cc1Cl]

(V)

is novel and especially developed for the process according to the invention and therefore constitute a further object of the invention.

In another preferred embodiment of the present invention the enantioselective reduction of the compound of formula V can be performed. Enantioselective hydrogenations of enamides are well precedented in the literature and frequently proceed in high yield and, when suitable chiral ligands are used, with good to excellent enantiomeric excess. In contrast thereto, no hydrogenations of N—OAlkyl enamides (compound 100, X═OAlky) are described in the prior art. The (1) enantioselective reduction of the olefinic bond and the (2) chemoselective of this reduction, avoiding the reduction of the nitrogen-oxygen bond are two requirements that have to be met simultaneously for the preparation of compound 1 b from the compound of formula V.

Reaction step d) can be performed by dissolving a metal catalyst (preferentially a Rhodium (I) or Ruthenium (II) complex, as for example: [Rh(cod)$_2$]OTf, [Rh(cod)$_2$]BF$_4$, [Ru(cod)$_2$]OTFA and [RuCl$_2$(p-cymene)]$_2$ and a suitable chiral ligand, preferentially a di-phosphine ligand as for example described under the Chemical Abstracts Entry Numbers CAS 133545-17-2, 150971-43-0, 76189-56-5, 74839-84-2, 155830-69-6, 184095-69-0, 1221745-90-9, 210842-74-3, 1003012-96-1, 387868-06-6, having the following formulae:

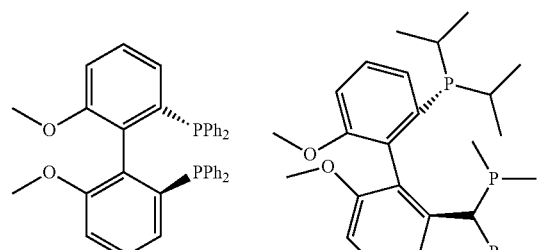

133545-17-2

150971-43-0

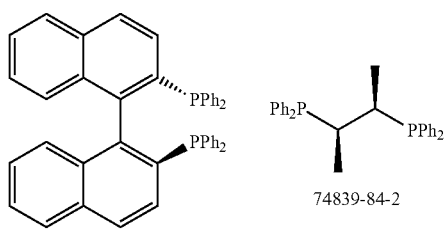

76189-56-5

74839-84-2

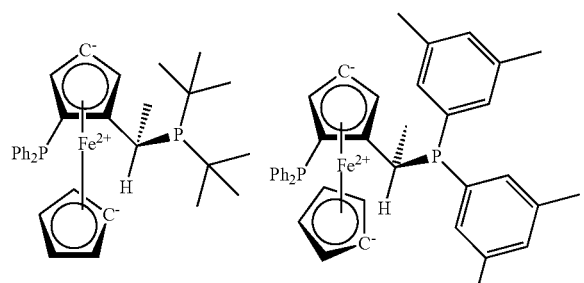

155830-69-6

184095-69-0

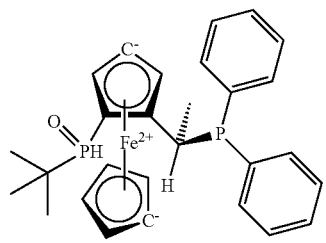

1221745-90-9

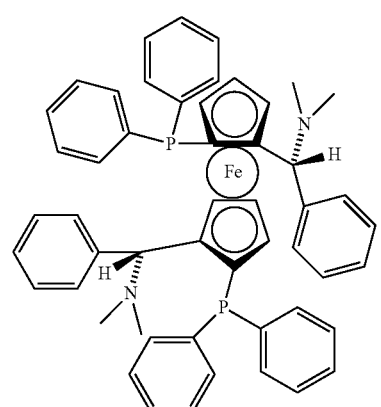

210842-74-3

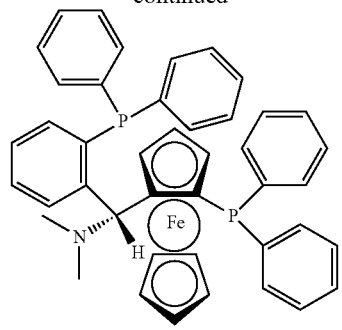

1003012-96-1

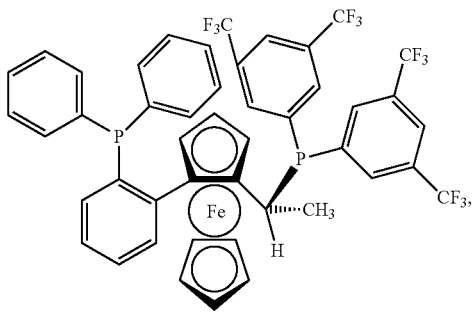

387868-06-6 in a suitable solvent or solvent mixture (typically derived from ethers such as dialkylethers, ethylene glycol, diethyleneglycol, tetrahydrofuran or dioxane and alkohols, such as methanol, ethanol, propanol, butanol and isopropanol).

Metal catalyst and ligand are used in a ratio ranging from 0.5 to 2, preferentially with ratios between 0.8 and 1.5. The catalytic system prepared in this manner is then combined with the compound of formula V (10 to 10000 excess) and transferred to a suitable reaction vessel, as for example a stainless steel autoclave, allowing the pressurization with hydrogen gas and rapid stirring. Pressures ranging from 0.1 bar to 15 MPa are required and the reaction time under those conditions may vary from 0.5 hours to 24 hours. Reaction temperatures may range from 20° C. to 200° C., preferred are temperatures in the range of 20° C. to 100° C. Typical safety precautions are applied when conduction such reactions. Alternative to the in-situ preparation of the catalytic system, an isolated metal-chiral ligand complex can be used. With such reaction conditions, the compound of formula Ib was obtained in up to 95% yield and with enantiomeric excess up to 95% (based on HPLC traces).

PREPARATORY EXAMPLES

Gcms

GCMS was conducted on a Thermo, MS: DSQ and GC: TRACE GC ULTRA with a column from Zebron phenomenex: Phase ZB-5 ms 15 m, diam: 0.25 mm, 0.25 µm, $H_2$ flow 1.7 ml/min, temp injector: 250° C., temp detector: 220° C., method: start at 70° C., 25° C./min until 320° C., hold 2 min at 320° C., total time 12 min. CI reagent gas: Methane, flow 1 ml/min.

Chiral HPLC Analysis: Method A

Autopurification System from Waters: 2767 sample Manager, 2489 UVNisible Detector, 2545 Quaternary Gradient Module. Column: Daicel CHIRALPAK® AS-3R, 3 µm, 0.46 cm×15 cm. Mobile phase: ACN/MeOH/Water 35/5/60. Flow rate: 1.0 ml/min. Detection: DAD Sample concentration: 1 mg/mL in ACN/Water 80/20. Injection: 5 μL.
Chiral HPLC Analysis: Method B
HPLC Waters UPLC—Hclass. DAD Detector Waters UPLC. Column: Daicel CHIRALPAK® IC, 3 μm, 0.46 cm×10 cm. Mobile phase: EtOH/MeOH 50/50. Flow rate: 1.0 ml/min. Detection: DAD. Sample concentration: 1 mg/mL in Hept/iPrOH 70/30. Injection: 24.

Example P1: preparation of enantiomerically enriched (2S)—N-methoxy-1-(2,4,6-trichlorophenyl)propan-2-amine of formula IIIa

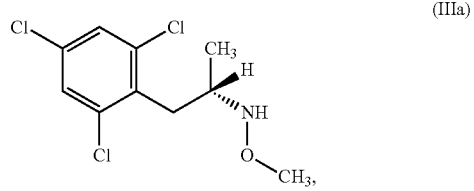

(IIIa)

Under an atmosphere of argon, (−)-norephedrine-(1R, 2S)-2-amino-1-phenyl-propan-1-ol-(76 mg, 0.5 mmol) was dissolved in tetrahydrofuran (5 ml) and cooled to 0° C. Borane-N,N-diethylaniline complex (0.18 ml, 0.5 mmol) was then added and the resulting mixture was stirred at 0° C. for 2 hours after which a solution of (E)-N-methoxy-1-(2,4,6-trichlorophenyl)propan-2-imine (0.267 g, 1 mmol) in 3 ml of tetrahydrofuran was added dropwise. Upon warming to 35° C., additional borane-N,N-diethylaniline complex (0.18 ml, 0.5 mmol) was added dropwise and the reaction mixture was then stirred for 2 hours at 35° C. and for 16 hours at ambient temperature. Upon quenching the reaction mixture with 1 ml methanol (dropwise addition) the volatile components were removed on a rotary evaporator and the mixture was treated with hydrochloric acid (10 ml, 2M) and stirred for 2 hours at ambient temperature.

The aqueous solution was subsequently washed with ether, basified with NaOH (2M) and extracted three times with tBuOMe. The organic layer was washed with brine, dried over sodium sulfate, and evaporated to give the enriched N-methoxyamine as a yellow oil (0.271 g, 0.827 mmol, 82% yield, estimated by quantitative HNMR)

$^1$HNMR: (CDCl$_3$, 400 MHz) δ: 0.91-0.93 (d, 3H); 2.72-2.77 (dd, 1H); 2.98-3.03 (dd, 1H); 3.25-3.30 (m, 1H); 3.93 (s, 3H); 7.15 (s, 2H).
Enantiomeric excess: Method A
R stereoisomer: Peak 1: 26.89 min; 3.94%
S Stereoisomer: Peak 2: 28.35 min; 96.06%

Example P2: Preparation of the Enantiomerically Enriched Compound of Formula Ib

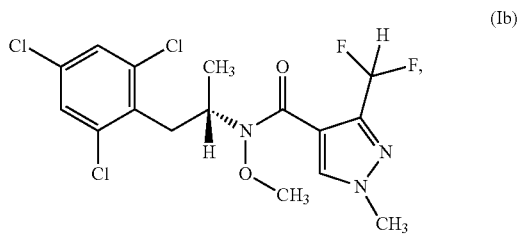 [SMILES: CON(C(=O)c1cn(C)nc1C(F)F)[C@@H](C)Cc1c(Cl)cc(Cl)cc1Cl]

(Ib)

A solution of 3-difluoromethyl-1H-pyrazole-4-carbonyl chloride (0.91 g; 4.7 mmol) in dichloromethane (5 ml) was added dropwise to a stirred solution of N-[2-(2,4-dichlorophenyl)-1-methyl-ethyl]-O-methlyhydroxylamine (1.0 g; 4.27 mmol)—prepared as described above—and triethylamine (0.90 ml; 6.4 mmol) in dichloromethane (7 ml) at 0° C. The cooling bath was removed and the reaction mixture was stirred for 1.5 hours at ambient temperature. The reaction mixture was then washed sequentially with 1M NaOH (20 ml), 1M HCl (20 ml), brine (20 ml) and then dried over sodium sulfate. After removal of the solvent the residue was purified by flash chromatography over silica gel (eluent: hexane/ethyl acetate 7:3) giving 1.35 g of 3-difluoromethyl-1-methyl-1H-pyrazole-4-carboxylic acid [2-(2,4-dichlorophenyl)-1-methyl-ethyl]-methoxy-amide as a white solid (m.p. 98-102° C.).

$^1$HNMR: (CDCl$_3$, 400 MHz): 1.41-1.46 (d, 3H); 2.99-3.04 (dd, 1H); 3.17-3.23 (dd, 1H); 3.60 (s, 3H); 3.95 (s, 3H); 4.68-4.70 (m, 1H); 7.10-7-62 (m, 5H). MS [M+H]+ 392/394/396.

In case of the acylation of the (S)-enriched O-methyl-N-[1-methyl-2-(2,4,6-trichlorophenyl)-ethyl]hydroxylamine the retentions times are (S)-stereoisomer (2.41 min), (R)-stereoisomer (2.97 min) and the enantiomeric ratio is conserved from (S)-enriched O-methyl-N-[1-methyl-2-(2,4,6-trichlorophenyl)-ethyl]hydroxylamine to (S)-enriched 3-difluoromethyl-1-methyl-1H-pyrazole-4-carboxylic acid [2-(2,4-dichlorophenyl)-1-methyl-ethyl]-methoxy-amide.

Example P3: Preparation of the Compound of Formula V

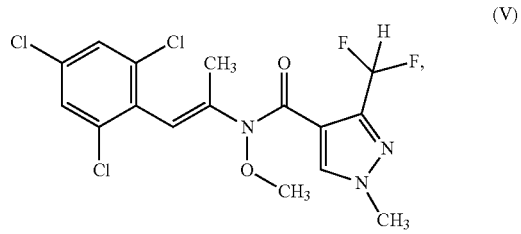 [SMILES: CON(C(=O)c1cn(C)nc1C(F)F)/C(C)=C/c1c(Cl)cc(Cl)cc1Cl]

(V)

The compound of formula II (a mixture of isomers E/Z=1:1.5) (2.67 g) was dissolved in THF (20 ml) under argon and cooled to −30° C. To this solution, a 0.5M toluene solution of KN(trimethylsilyl)$_2$ (40 ml) was added at a rate allowing the temperature to stay below −25° C. The resulting solution was stirred for additional 10 min and the compound of formula VI (3.89 g) dissolved in THF (10 ml) was added at a rate allowing the temperature to stay below −20° C. The resulting solution was stirred for 0.3 hours at −20 to −30° C. A saturated aqueous solution of NH4Cl (100 ml) was added, the reaction was stirred an additional 10 min. The resulting mixture was extracted with EtOAc (2×70 ml) and the combined organic layers were washed with brine, then dried over Na$_2$SO$_4$ and concentrated under vacuum. The resulting brown mass was purified by flash chromatography (silica gel, EtOAc: heptan=1:1). The product containing fractions were concentrated under vacuum and the resulting oil was crystallized from ether to give colorless crystals (1.93 g) of compound V. This reaction is very selective towards the (E)-isomer, as the (Z)-isomer of compound of formula V is not observed in significant amount after the reaction.

1H NMR (CDCl3, 500 MHz) δ=7.94 (t, J=1.46 Hz, 1H); 7.39 (s, 1H); 7.30 (t, J=54.20 Hz, 1H); 6.41 (s, 1H); 4.00 (s, 3H); 3.82 (s, 3H); 1.91 (s, 3H).

Example P4: Preparation of the Enantiomerically Enriched Compound of Formula Ib

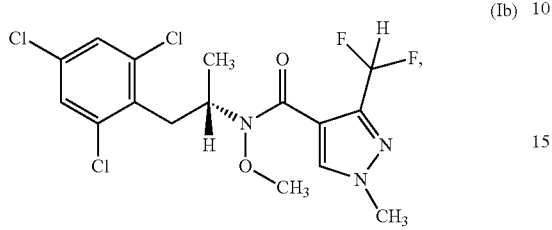

16.9 mg (0.031 mmol) SL-J002-1 and 10.6 mg (0.028 mmol) [Rh(nbd)$_2$]BF$_4$ were placed in a 10 ml Schlenk flask that was previously set under an atmosphere of argon. Then 4 ml degassed methanol was added and this orange solution stirred for 30 min at room temperature. In a second 25 ml Schlenk flask, 0.3 g (0.706 mmol) of compound V was placed, followed by 3.5 ml degassed THF and 10 ml degassed MeOH. The clear solution was stirred for 10 min. Then, both the substrate and the catalyst solution were transferred via cannula into a 50 ml stainless steel reactor that was previously set under an atmosphere of argon. The reactor was sealed, purged with argon in three cycles (1 bar/20 bar) and finally, the argon replaced by hydrogen (4 cycles 0.1 MPa/2 MPa). The reactor pressure was set to 5 MPa hydrogen, heating to 50° C. and stirring started. IPC sample have been collected after 1.5 hours, 6 hours and 21 hours. After 48 hours reaction time, the pressure was released. The crude product was analyzed with respect to conversion, chemoselectivity and enantiomeric excess using the HPLC. The conversion after 48 hours was 99.8%, product Ib was formed with 87% chemoselectivity and 69% enantiomeric excess.

$^1$HNMR: (CDCl$_3$, 400 MHz):
1.41-1.46 (d, 3H); 2.99-3.04 (dd, 1H); 3.17-3.23 (dd, 1H); 3.60 (s, 3H); 3.95 (s, 3H); 4.68-4.70 (m, 1H); 7.10-7-62 (m, 5H).
MS [M+H]+ 392/394/396.

What is claimed is:

1. A process for the enantioselective preparation of the compound of formula (Ib)

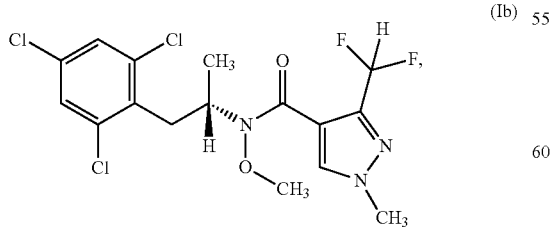

which process comprises
a) reducing the (E)- or (Z)-form of a compound of formula (II)

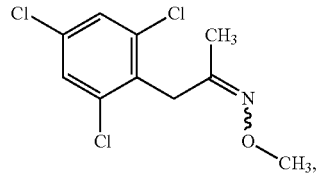

with an enantioselective reagent to give a compound of formula (IIIa)

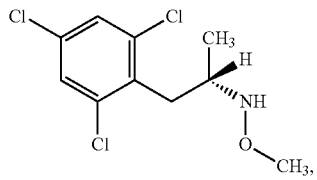

and
b) acylating the compound of formula (IIIa) with the compound of formula (IV)

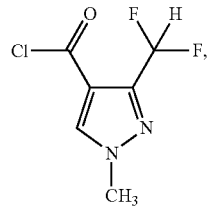

or
c) coupling the compound of formula (IV) with the compound of formula (II), to give a compound of formula (V)

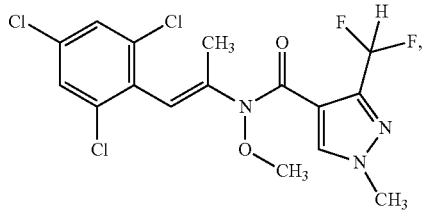

and
d) reducing the compound of formula (V) in the presence of hydrogen, a catalyst and a chiral ligand, to give the compound of formula (Ib).

2. The process for the enantioselective preparation of the compound of formula (Ib) according to claim 1, which process comprises
a) reducing the (E)- or (Z)-form of a compound of formula (II)

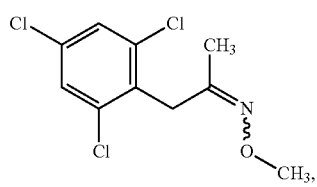

with an enantioselective reagent to a compound of formula (IIIa)

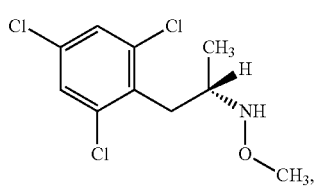

and b) acylating the compound of formula (IIIa) with the compound of formula (IV)

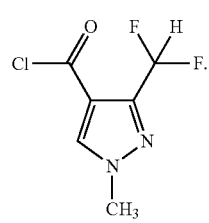

3. The process for the enantioselective preparation of the compound of formula (Ib) according to claim 1, which process comprises c) coupling the compound of formula (IV) with the compound of formula (II), to give a compound of formula (V)

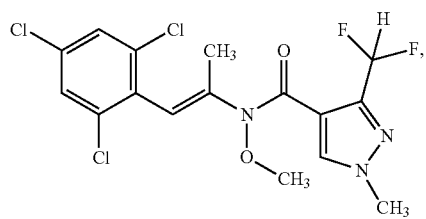

and d) reducing the compound of formula (V) in the presence of hydrogen, a catalyst and a chiral ligand, to the compound of formula (Ib).

4. The process for the enantioselective preparation of the compound of formula (Ib) according to claim 1,

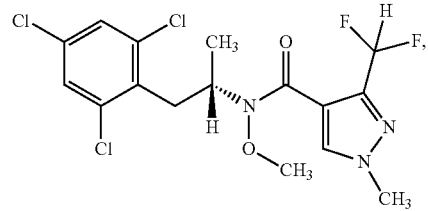

which process comprises a) reducing the (E)- or (Z)-form of a compound of formula (II)

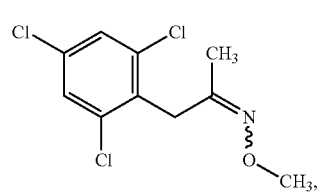

with a borane complex as a reducing agent, in the presence of a single enantiomer of a chiral 1,2-aminoalcohol, in an inert solvent and at temperatures ranging from 0° C. and 60° C., to a compound of formula (IIIa)

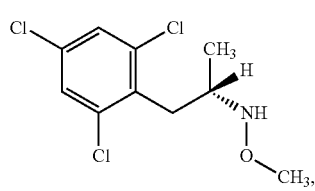

and b) acylating the compound of formula (IIIa) with the compound of formula (IV), in an inert solvent, in the presence of a weak base and at temperatures ranging between −20° C. and 120° C.

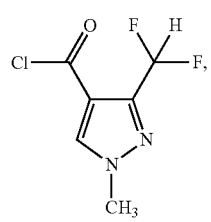

or c) coupling the compound of formula (IV) with the compound of formula (II), by deprotonation of compound of formula (II) with 1 to 5 equivalents of a suitable base in an inert aprotic solvent, wherein the suitable base is selected from KN(iPr)$_2$, LiN(iPr)$_2$, KN(trimethylsilyl)$_2$, BuLi, and KN(iPr)$_2$/KOtBu, at temperature ranging from −78° C. to 25° C., followed by treatment with compound of formula (IV), to give a compound of formula (V),

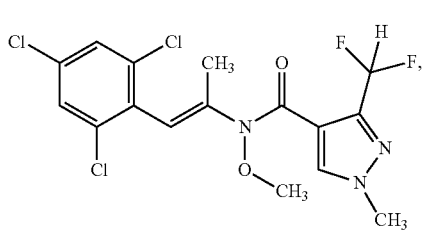

(V)

and d) reducing the compound of formula (V) in the presence of hydrogen at pressures ranging from 0.1 bar to 15 MPa, in the presence of 0.1 to 0.0001 equivalent of a metal catalyst and a single enantiomer of a suitable chiral ligand, in ratio of metal catalyst to chiral ligand ranging from 0.8 to 1.5, in a suitable solvent and at temperatures ranging from 20° C. to 100° C., to give the compound of formula (Ib).

5. The compound of formula (V)

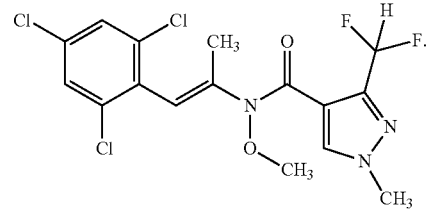

(V)

6. The process of claim 2, wherein the reduction of the compound of formula (II) is performed via the action of borane in the presence of a single enantiomer of a chiral amino-alcohol.

7. The process according to claim 6, wherein the source of borane is borane diethylaniline.

* * * * *